United States Patent
Chapman et al.

(10) Patent No.: US 9,447,525 B2
(45) Date of Patent: Sep. 20, 2016

(54) ON-LINE DETECTION OF DEFECTS IN FIBROUS MEMBERS

(71) Applicant: Eastman Chemical Company, Kingsport, TN (US)

(72) Inventors: Peter Chapman, Kingsport, TN (US); Steven F. Wright, Johnson City, TN (US); James E. Grant, Jr., Johnson City, TN (US)

(73) Assignee: Eastman Chemical Company, Kingsport, TN (US)

( * ) Notice: Subject to any disclaimer, the term of this patent is extended or adjusted under 35 U.S.C. 154(b) by 278 days.

(21) Appl. No.: 14/182,954

(22) Filed: Feb. 18, 2014

(65) Prior Publication Data

US 2015/0233888 A1    Aug. 20, 2015

(51) Int. Cl.
| | |
|---|---|
| *D01G 31/00* | (2006.01) |
| *G01N 33/36* | (2006.01) |
| *D04H 1/74* | (2006.01) |
| *D01H 4/00* | (2006.01) |

(52) U.S. Cl.
CPC ............. *D01G 31/00* (2013.01); *D01H 4/00* (2013.01); *D04H 1/74* (2013.01); *G01N 33/365* (2013.01)

(58) Field of Classification Search
CPC .......... D01G 31/00; D04H 1/74; D01H 4/00; G01N 33/365
See application file for complete search history.

(56) References Cited

U.S. PATENT DOCUMENTS

| | | | | | |
|---|---|---|---|---|---|
| 3,106,762 | A | * | 10/1963 | Solanich | B65H 63/064 28/227 |
| 3,792,821 | A | * | 2/1974 | Fallon | B65H 54/026 226/11 |
| 3,999,695 | A | * | 12/1976 | Bradley | B26D 5/28 19/25 |

(Continued)

FOREIGN PATENT DOCUMENTS

| | | |
|---|---|---|
| EP | 0 493 050 B1 | 7/1992 |
| FR | 2200504 A1 | 4/1974 |

(Continued)

OTHER PUBLICATIONS

Notification of Transmittal of the International Search Report and the Written Opinion of the International Searching Authority, or the Declaration date of mailing Apr. 21, 2015 received in corresponding International Patent Application No. PCT/US2015/015164.

(Continued)

*Primary Examiner* — Shaun R Hurley
(74) *Attorney, Agent, or Firm* — Hovey Williams LLP

(57) ABSTRACT

An on-line defect detection system for detecting a defect in a fibrous member and related processes are provided. The defect detection system may include first and second fiber contacting members where at least one of the contacting members is shiftable relative to the other contacting member. The defect detection system may also include a defect detection zone defined between at least a portion of the first and second fiber contacting members. The defect detection zone may be configured to receive at least a portion of the fibrous member in a manner such that the fibrous member contacts the first and second fiber contacting members in the defect detection zone. Further, the defect detection zone may also include a sensor configured to sense movement of one of the first and second fiber contacting members and generate an electronic signal based on the sensed movement of the at least one fiber contacting member.

40 Claims, 10 Drawing Sheets

(56) References Cited

U.S. PATENT DOCUMENTS

| | | |
|---|---|---|
| 4,189,841 A | 2/1980 | Loepfe |
| 4,413,637 A * | 11/1983 | Irving .................... A24C 5/343 |
| | | 131/66.1 |
| 4,924,406 A * | 5/1990 | Bergamini ........... B65H 63/065 |
| | | 250/559.24 |
| 4,938,268 A | 7/1990 | Shaw |
| 5,216,921 A | 6/1993 | Tsuboi |
| 5,237,754 A * | 8/1993 | Oexler .................... D01H 5/38 |
| | | 19/23 |
| 6,185,833 B1 * | 2/2001 | Bravdo .................... G01B 7/06 |
| | | 33/783 |
| 7,304,726 B2 | 12/2007 | Kaneda et al. |
| 7,585,441 B2 | 9/2009 | Caenen et al. |
| 2013/0005061 A1 | 1/2013 | Shim |
| 2013/0014557 A1 | 1/2013 | Lee |

FOREIGN PATENT DOCUMENTS

| | | |
|---|---|---|
| FR | 2957675 A1 | 9/2011 |
| GB | 2 435 325 A | 8/2007 |

OTHER PUBLICATIONS

Tumajer, Petr, et al, "Use of the Vibtex Vibrations System for Testing Textiles," AUTEX Research Journal, vol. 11, No. 2, Jun. 2011, pp. 47-53.

* cited by examiner

ON-LINE DETECTION OF DEFECTS IN FIBROUS MEMBERS

FIELD OF THE INVENTION

This invention relates generally to the production of multi-fiber articles. More particularly, this invention relates to a system for detecting a defect in a fibrous member that is to be formed into a multi-fiber article.

BACKGROUND

Generally, the quality of certain multi-fiber articles may depend upon the quality of the individual fibrous members that make up that multi-fiber article. For example, if individual tows having various defects are combined into a tow band, the properties of that tow band may be adversely affected. Generally, defects in individual tows can arise during the formation of the tow. For example, while spinning individual filaments into a tow, several filaments may join together prematurely prior to complete curing, which can result in a defect known as spinning machine harsh. Tow bands having individual tows exhibiting spinning machine harsh can produce an undesirable product, e.g., a tow band having a lower pressure drop variability. For this and other reasons, a manufacturer of tow may manually inspect a sample of tow to determine if spinning machine harsh is present. However, such an inspection technique is labor intensive and typically results in the monitoring of only a small percentage of the tow being produced. Further, the manual inspection process can be destructive to the sample thereby causing a loss of product. Therefore, there is a need for a system and/or an improved process for detecting a defect in a fibrous member that is less labor intensive, and that can monitor a substantial portion of the product being produced.

SUMMARY

In one embodiment of the present invention, an on-line defect detection system is provided for detecting a defect in an elongated continuous fibrous member during transferring of the fibrous member from a fiber producing machine to a fiber combining machine. The defect detection system includes a first fiber contacting member, and a second fiber contacting member, where at least one of the first and second fiber contacting members is shiftable relative to the other of the first and second fiber contacting members. The system also includes a defect detection zone defined between at least a portion of the first and second fiber contacting members, where the defect detection zone is configured to receive at least a portion of the fibrous member in a manner such that the fibrous member contacts the first and second fiber contacting members in the defect detection zone. Further, the system includes a sensor configured to (i) sense movement of at least one of the first and second fiber contacting members and (ii) generate an electronic signal based on the sensed movement of the at least one fiber contacting member.

In another embodiment of the present invention, an on-line defect detection process is provided. The process includes (a) producing a continuous elongated fibrous member in a fiber forming machine, (b) passing the fibrous member through a defect detection zone, where the passing includes contacting substantially opposite sides of the fibrous member with first and second fiber contacting members, where variations in the width of the fibrous member causes shifting of at least one of the first and second contact members relative to the other of the first and second contact members, (c) sensing shifting of at least one of the first and second fiber contacting members relative to the other of the first and second fiber contacting members, and (d) generating an electronic signal based on the sensed shifting of step (c).

In yet another embodiment of the present invention there is provided a multi-fiber article production system that includes a fiber source, at least one spinning machine configured to form at least a portion of the fiber source into a tow, and a tow combining machine configured to combine a plurality of the tows into a tow band. The system further includes a first tow contacting member, and a second tow contacting member, where at least one of the first and second tow contacting members is shiftable relative to the other of the first and second tow contacting members. The system also includes a defect detection zone defined between at least a portion of the first and second tow contacting members, where the defect detection zone is configured to receive at least a portion of the tow in a manner such that the tow contacts the first and second tow contacting members in the defect detection zone, and a sensor configured to (i) sense movement of at least one of the first and second tow contacting members and (ii) generate an electronic signal based on the sensed movement of the at least one tow contacting member.

BRIEF DESCRIPTION OF THE FIGURES

Embodiments of the present invention are described herein with reference to the following drawing figures, wherein.

DETAILED DESCRIPTION

Figure 1:
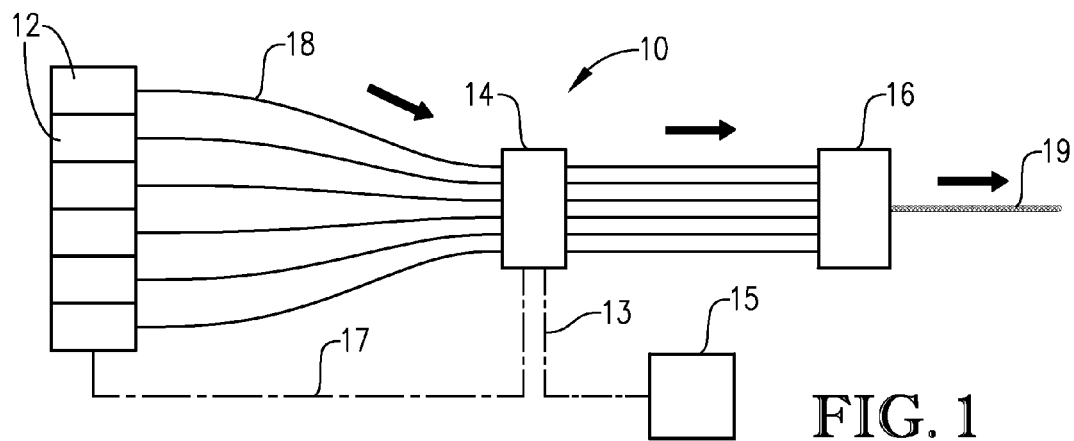
FIG. 1 is a schematic diagram of an exemplary multi-fiber article production system in accordance with one embodiment of the present invention.

FIG. 1 depicts a multi-fiber article production system 10 that can include a plurality of fiber producing machines 12, a defect detection system 14, and a fiber combining machine 16. In the embodiment depicted in FIG. 1, the multi-fiber article production system 10 may begin with the production of a continuous elongated fibrous member 18 produced in the fiber producing machine 12. In certain embodiments, each fiber producing machine 12 may produce an individual fibrous member 18.

The fibrous member 18 may be any type of fibrous member known to one skilled in the art, as long as such a fibrous member is capable of being combined into a multi-fiber article 19. In certain embodiments, the fibrous member 18 may comprise multiple individual filaments. In certain other embodiments, the fibrous member 18 may be a monofilament fiber. In one or more embodiments, the fibrous member 18 may be a yarn or a tow.

In certain embodiments, the fibrous member 18 may be a tow comprising a plurality of individual filaments. In one or more embodiments, the tow may be derived from cellulose. In certain embodiments, the tow may comprise cellulose acetate. In one or more embodiments, the tow may have an averaged diameter of at least $\frac{1}{64}^{th}$ of an inch, $\frac{1}{32}^{nd}$ of an inch, or $\frac{1}{8}^{th}$ of an inch, and/or not more than 2 inches, 1 inch, or ½ of an inch. In certain embodiments, the tow may be formed of at least 1, 500, or 5,000 individual filaments, and/or not more than 100,000, 50,000, or 35,000 individual filaments. In one or more embodiments, the individual filaments may have an averaged diameter of at least 1 μm, 10 μm, or 20 μm, and/or not more than 1000 μm, 100 μm, or 50 μm.

Returning now to FIG. 1, as discussed above, the fibrous member 18 may be produced in a fiber producing machine 12. The fiber producing machine 12 can be any type of machine known to one skilled in the art that is capable of forming a continuous elongated fibrous member from a fiber source. In certain embodiments, the fiber producing machine 12 can be a spinning cabinet or spinning machine.

As shown in the embodiment depicted in FIG. 1, the multi-fiber production system 10 may include a plurality of individual fiber producing machines 12. In certain embodiments, the system 10 may include at least 2, 5, 10, or 15 individual fiber producing machines 12, and/or not more than 100, 75, 50, or 40 individual fiber producing machines 12. In one or more embodiments, the system 10 may include about 20 individual fiber producing machines 12. In certain embodiments, such as that depicted in FIG. 1, each individual fiber producing machine 12 may produce at least one fibrous member 18.

In one or more embodiments, the multi-fiber production system 10 may include an on-line defect detection system, e.g., the defect detection system 14 of FIG. 1, which may be configured to monitor the fibrous members 18 for defects during the multi-fiber article production process. For example, in certain embodiments, prior to combining the fibrous members 18 into a multi-fiber article 19, the fibrous members 18 may be exposed to at least a portion of the defect detection system 14. In the embodiment depicted in FIG. 1, after exiting the fiber producing machines 12 and prior to entering the fiber combining machine 16, the fibrous members 18 may be exposed to the defect detection system 14. The defect detection system 14 can be positioned anywhere within the multi-fiber article production system 10 as long as the fibrous members 18 are exposed to at least a portion of the defect detection system 14 prior to being formed into a multi-fiber article 19. For example, as discussed below, in certain embodiments, at least a portion of the defect detection system 14, may be coupled to an individual fiber forming machine 12.

In certain embodiments, as discussed in detail below, the defect detection system 14 may be configured to monitor a fibrous member 18 in such a manner so as to be able to detect a defect in that fibrous member 18. In one or more embodiments, the defect may be characterized by an increased width of the fibrous member 18. In certain embodiments, the defect may be spinning machine harsh. In such embodiments, when a defect is detected, a communication signal 13 may be sent from the defect detection system 14 to a defect warning system 15 to thereby alert an operator of such a defect. In the same or alternative embodiments, when a defect is detected, the defect detection system 14 may transmit a signal 17 to one or more fiber producing machines 12 which may cause one or more fiber producing machines 12 to automatically turn off. The communication signals 13 and 17 can be any type of signal capable of relaying information or a command from the defect detection system 14 to the defect warning system 15 and the fiber producing machines 12. For example, in certain embodiments, signals 13 and 17 may include an electronic signal transmitted through a wire/line, or may include a wireless based signal.

In the embodiment depicted in FIG. 1, after the fibrous members 18 exit the fiber producing machine 12 and pass through the defect detection system 14, the fibrous members 18 may be combined into a multi-fiber article 19 via the fiber combining machine 16. The fiber combining machine 16 can be any type of machine known to one skilled in the art that is capable of combining more than one fibrous member 18 into a multi-fiber article 19. In certain embodiments, the fiber combining machine 16 may be configured to combine at least 2, 8, or 17 fibrous members, and/or not more than 100, 50, or 20 fibrous members into a multi-fiber article 19. In one or more embodiments, the fiber combining machine 16 may be configured to produce a multi-fiber article 19 selected from the group consisting of a band, a yarn, a woven article, and a nonwoven article. In certain embodiments, the fiber combining machine 16 may be configured to combine a plurality of tows into a tow band.

Figure 2:
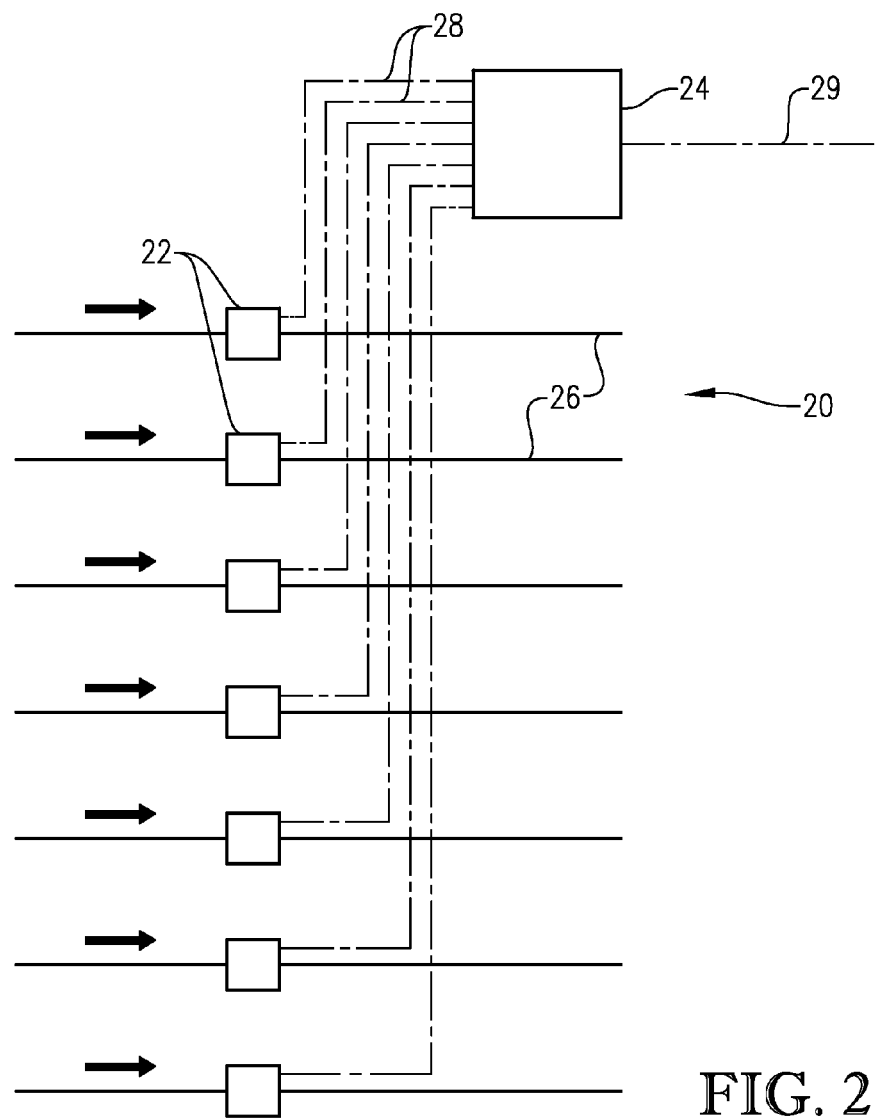
FIG. 2 is a schematic diagram of an exemplary defect detection system in accordance with one embodiment of the present invention.

FIG. 2 depicts one embodiment of a defect detection system 20 that may include a plurality of defect detection modules 22 and a data processing system 24. In certain embodiments, the defect detection system 20 may be configured to monitor individual fibrous members 26. For example, in the embodiment depicted in FIG. 2, a single defect detection module 22 can be configured to monitor one continuous elongated fibrous member 26 as the fibrous member 26 is produced and transported for further processing.

In certain embodiments, such as that depicted in FIG. 2, each detection module 22 may send an electronic signal 28 to the data processing system 24 to relay data obtained from the monitoring of a fibrous member 26. In certain embodiments, the electronic signal 28 may be transmitted through a wire/line to the data processing system 24 and/or it may be converted to a wireless based signal and sent to the data processing system 24 via wireless technology.

The data processing system 24 of FIG. 2 may be configured to receive the electronic signal 28 from at least one defect detection module 22, and based on that signal determine whether a defect is present in the monitored fibrous member 26. For example, as discussed in detail below, the data processing system 24 may collect and monitor data obtained from each of the individual detection modules 22 for a given period of time and determine if there is any indication of a defect on any of the fibrous members 26 being monitored.

In the embodiment depicted in FIG. 2, the data processing system 24 may transmit a communication signal 29, e.g., to an operator in order to communicate information about the monitored fibrous members 26. The communication signal 29 can be any type of signal known to one skilled in the art, such as, for example, an electronic signal transmitted via a line, or a wireless-based signal.

Figure 3:
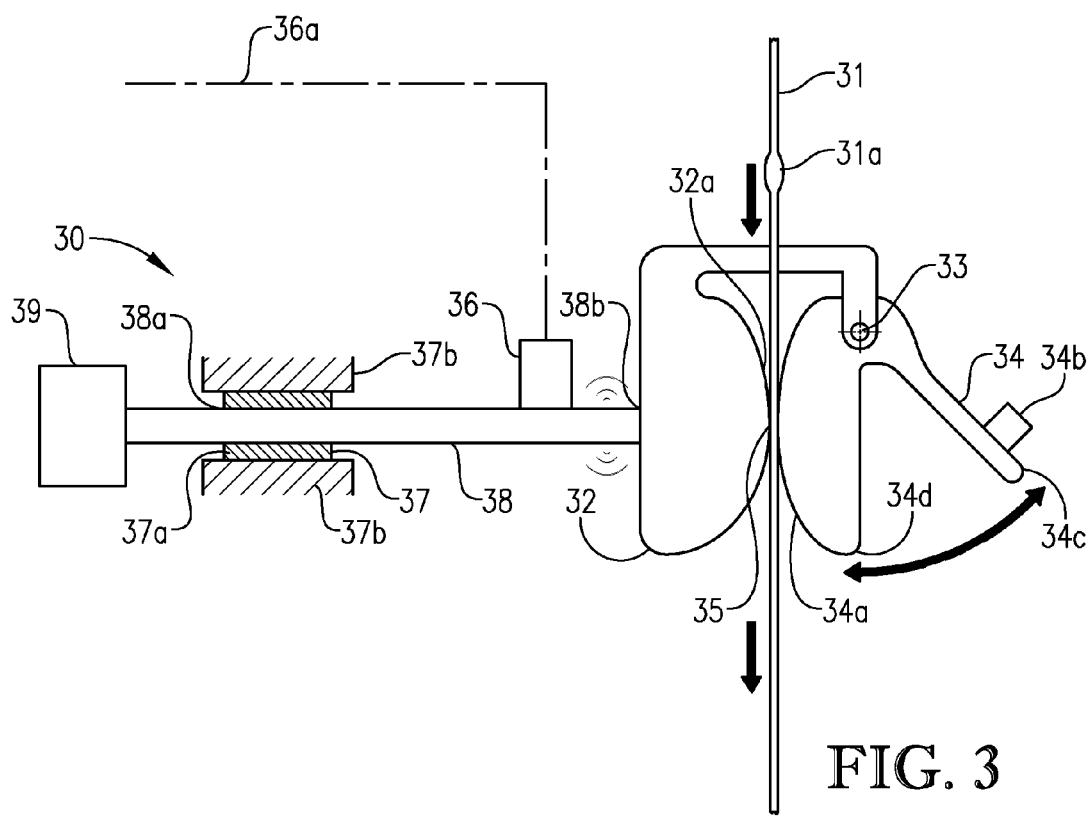
FIG. 3 is a side view of a defect detection module in accordance with one embodiment of the present invention, particularly showing a first fiber contacting member coupled to an elongated support member, a second fiber contacting member pivotally coupled to the first fiber contacting member, a fibrous member positioned between the first and second fiber contacting members, and a sensor coupled to the elongated support member.

FIG. 3 depicts one embodiment of a defect detection module 30 that may include a first fiber contacting member 32, a second fiber contacting member 34, a sensor 36, and an elongated support member 38. In certain embodiments, the elongated support member 38 may be coupled to at least one of the contacting members 32 and 34. For example, in the embodiment depicted in FIG. 3, the first fiber contacting member 32 may be coupled to the elongated support member 38. The elongated support member 38 may be coupled to at least one of the contacting members 32 and 34 in any manner known to one skilled in the art and a particular manner may be chosen for a specific purpose. In one or more embodiments, the fiber contacting members 32 and 34, and the elongated support member 38, may be made from any material, such as, for example, a metal material, a plastic material, a ceramic material, or a combination thereof.

In certain embodiments, one of the contacting members 32 or 34 may be shiftable relative to the other of the contacting members 32 or 34. For example, in the embodiment depicted FIG. 3, the contacting member 32 may be coupled to the elongated support member 38 in a fixed position while the contacting member 34 may be pivotally coupled to the contacting member 32 via a hinge 33. The hinge 33 can be any type of hinge as long as the hinge allows the contacting member 34 to shift relative to the contacting member 32, and a particular hinge can be chosen for a specific purpose by one of skilled in the art.

In one or more embodiments, at least a portion of the contacting members 32 and 34 may define a defect detection zone 35 that is configured to receive at least a portion of a fibrous member 31 in a manner such that the fibrous member 31 contacts both contacting members 32 and 34. For example, as shown in the embodiment depicted in FIG. 3, a portion of the contacting members 32 and 34 each present a convex surface 32a and 34a, respectively, that is in contact with the fibrous member 31 as the fibrous member 31 passes through the defect detection zone 35.

In certain embodiments, the contacting members 32 and 34 may be biased towards one another. In one or more embodiments, the contacting members 32 and 34 may be gravity biased towards one another. For example, in the embodiment depicted in FIG. 3, the second fiber contacting member 34 may include a weight 34b on one arm 34c of the contacting member 34. In such embodiments, due to the force of gravity, the weight 34b may cause the contacting member 34 to pivot about the hinge 33 and maintain the convex surface 34a on arm 34d of the contacting member 34 in contact with, or in a resting position near, the convex surface 32a of the first fiber contacting member 32.

As discussed above, the defect detection system 30 of FIG. 3 includes a sensor 36. The sensor 36 can be any type of sensor that is capable of detecting a defect in the fibrous member 31, and a specific sensor can be chosen by one skilled in the art for a particular purpose. In certain embodiments, the sensor 30 may be selected from the group consisting of an optical sensor, an electromagnetic sensor, an acoustical sensor, a mechanical sensor, an electrical sensor, and a combination thereof. In one or more embodiments, the sensor 36 may be an accelerometer. In certain embodiments, the sensor 36 may be an integrated electronics piezo electric accelerometer.

In various embodiments, while operating the defect detection module 30, it may be positioned in such a manner that the module 30 may be subjected to vibrations from an adjacent fiber forming machine, fiber combining machine, and/or other equipment used in the production of a multi-fiber article. Thus, in certain embodiments, it may be desirable to minimize any background vibration or movement of the defect detection module 30 so that the sensor 36 can more accurately detect a defect in the fibrous member 31. In such embodiments, the defect detection module 30 may include a dampening member 37. For example, in the embodiment depicted in FIG. 3, the defect detection module 30 may include a dampening material 37a positioned between the elongated support member 38 and a rigid member 37b that may be subjected to background vibrations or movements. In one or more embodiments, the rigid member 37b may be a component of a multi-fiber production system, such as, for example, a rigid surface of a fiber producing machine or a fiber combining machine, or the rigid member 37b may be a portion of a rigid base of the defect detection module 30 not shown in FIG. 3. The dampening material 37a can be any type of material that is capable of minimizing the background vibration or movement of the defect detection module 30. For example, in certain embodiments, the dampening material 37a may include a silicone material, a rubber material, or a combination thereof.

In one or more embodiments, the dampening member 37 may be positioned on the defect detection module 30 in such a manner that it may reduce at least a portion of background vibrations while not interfering with the ability of the sensor 36 to detect a defect in the fibrous member 31. In such embodiments, the dampening member 37 may be positioned to dampen vibrations coming from the rigid member 37b while not dampening the sensing of vibrations coming from the fiber contacting members 32 and 34. Further, in such embodiments, the sensor 36 may be coupled to the elongated support member 38 at a position between where the dampening member 37 is coupled to the elongated support member 38 (at position 38a), and where at least one of the contacting members 32 and 34 is coupled to the elongated support member 38 (at position 38b). Other configurations of a dampening member 37 are within the scope of the present invention as long as such a dampening member is capable of minimizing background vibrations coming from a source other than the sensing of the fibrous member 31.

As discussed above, in certain embodiments, the defect detection module 30 may be coupled to at least a portion of a component of a multi-fiber production system via a rigid member 37b. In such embodiments, it may be beneficial for the defect detection module 30 to include a counter balance 39 in order to provide stability to the fiber contacting members 32 and 34, and the module 30 in general. For example, in the embodiment depicted in FIG. 3, a counter balance 39 is coupled to the elongated support member 38. Further, as shown in the embodiment depicted in FIG. 3, the counter balance 39 and the contacting members 32 and 34 are positioned at opposing ends of the elongated support member 38.

In certain embodiments, the defect detection module 30 of FIG. 3 may be configured to detect a defect, e.g., defect 31a, in the fibrous member 31. In such embodiments, the fibrous member 31 may pass through the defect detection zone 35 contacting substantially opposite sides of the fibrous member 31 with the fiber contacting members 32 and 34. Further, in such embodiments, a defect, e.g., defect 31a, may cause the shifting of at least one of the fiber contacting members 32 and 34 relative to the other of the fiber contacting members 32 and 34. In such embodiments, the sensor 36 may detect the shifting of at least one of the fiber contacting members 32 and 34. In addition, in such embodiments, the sensor 36 may continuously or intermittently generate and/or transmit an electronic signal 36a to communicate a parameter sensed by the sensor 36 to a data processing system or an operator. In certain embodiments, the defect detection module 30 may simultaneously have a fibrous member 31 pass through the defect detection zone 35, sense the shifting of at least one of the fiber contacting members 32 and 34, and generate an electronic signal based on the sensed shifting of one of the fiber contacting members 32 and 34.

In one or more embodiments, after the fibrous member 31 has passed through the defect detection zone 35, a plurality of fibrous members, including the fibrous member 31, may be combined in a fiber combining machine to produce a multi-fiber article.

Figure 4:
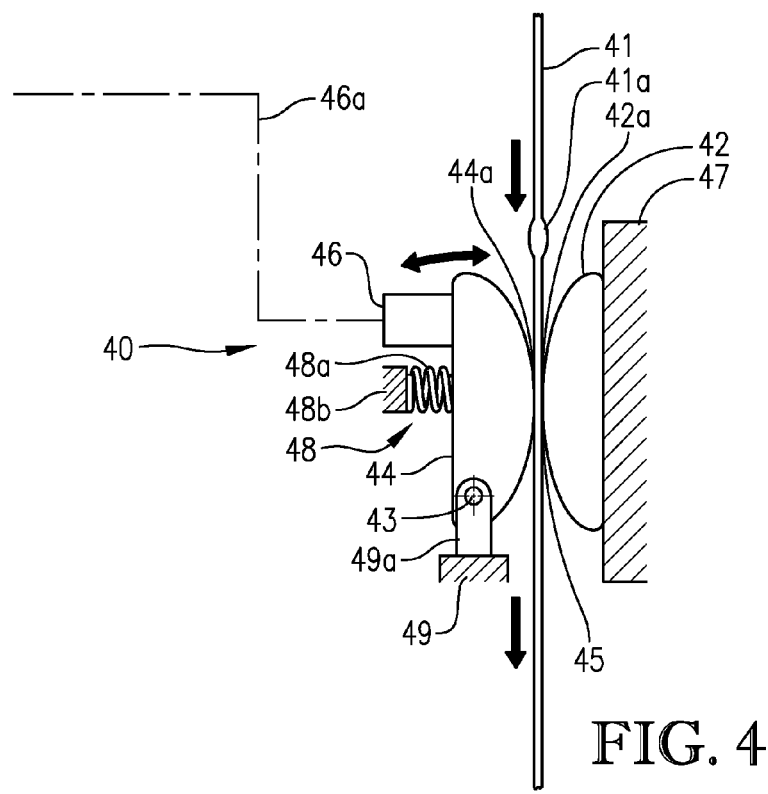
FIG. 4 is a side view of a defect detection module in accordance with another embodiment of the present invention, particularly showing a first fiber contacting member secured to a first rigid member, a second fiber contacting member pivotally coupled to a second rigid member, a sensor coupled to the second fiber contacting member, a biasing member coupled to the second fiber contacting member, and a fibrous member positioned between the first and second fiber contacting members.

FIG. 4 depicts one embodiment of a defect detection module 40 that includes a first fiber contacting member 42, a second fiber contacting member 44, a sensor 46, and a biasing member 48. The contacting members 42 and 44 may be made from any material, such as, for example, a metal material, a plastic material, a ceramic material, or a combination thereof.

In the embodiment depicted in FIG. 4, the first fiber contacting member 42 may be coupled to a rigid member 47. The rigid member 47 may be any type of rigid member, as long as the second fiber contacting member 42 can be coupled thereto in a fixed position. In certain embodiments, the second fiber contacting member 44 may be pivotally coupled to a rigid member 49. The rigid member 49 may be any type of rigid member, as long as the second fiber contacting member 44 can be pivotally coupled thereto. In certain embodiments, the rigid members 47 and/or 49 may be components of a multi-fiber production system, such as, for example, a rigid surface of a fiber producing machine or a fiber combining machine, or the rigid members 47 and/or 49 may be a portion of a rigid base of the defect detection module 40 not shown in FIG. 4.

As mentioned above, the second fiber contacting member 44 of FIG. 4 may be pivotally coupled to the rigid member 49 via a hinge 43. The hinge 43 can be any type of hinge as long as such a hinge allows the second fiber contacting member 44 to shift relative to the first fiber contacting member 42, and a particular hinge can be chosen for a specific purpose by one skilled in the art. In one or more embodiments, such as that depicted in FIG. 4, the rigid member 49 may include a hinge extension member 49a to thereby provide a space for the contacting member 44 to more freely pivot without contacting the rigid member 49. The hinge extension member 49a can be any type of member as long as such a member is capable of providing a space for the contacting member 44 to freely pivot. In certain embodiments, the hinge extension member 49a may be integral with the rigid member 49.

In certain embodiments, the defect detection module 40 of FIG. 4 may include a biasing member 48 to bias the contacting members 42 and 44 toward one another. The biasing member 48 may be any type of biasing member that is capable of causing the contacting members 42 and 44 to be biased towards one another. In the embodiment depicted in FIG. 4, the biasing member 48 may include a spring 48a that biases the second fiber contacting member 44 towards the first fiber contacting member 42. The spring 48a of FIG. 4, may be coupled to a rigid member 48b. The rigid member 48b can be any rigid member capable of having a spring 48a coupled thereto. In certain embodiments, the rigid member 48a may be a component of a multi-fiber production system, such as, for example, a rigid surface of a fiber producing machine or a fiber combining machine, or the rigid member 48a may be a portion of a rigid base of the defect detection module 40 not shown in FIG. 4.

In one or more embodiments, at least a portion of the contacting members 42 and 44 may define a defect detection zone 45 that is configured to receive at least a portion of a fibrous member 41 in a manner such that the fibrous member 41 contacts both contacting members 42 and 44. For example, as shown in the embodiment depicted in FIG. 4, a portion of the contacting members 42 and 44 each present a convex surface 42a and 44a, respectively, that is in contact with the fibrous member 41 as the fibrous member 41 passes through the defect detection zone 45.

As discussed above, the defect detection module 40 of FIG. 4 may include a sensor 46. In the embodiment depicted in FIG. 4, the sensor 46 may be coupled to the second fiber contacting member 44. The sensor 46 can be coupled to the contacting member 44 in any way known to one skilled in the art as long as the sensor 46 is capable of detecting a defect in a fibrous member 41. In certain embodiments, the sensor 46 may have the same parameters as the sensor 36 discussed above with reference to the defect detection module 30 of FIG. 3. For example, in certain embodiments, the sensor 46 may be an accelerometer.

In certain embodiments, the defect detection module 40 may operate so as to detect a defect, e.g., defect 41a, in the fibrous member 41 as the fibrous member 41 passes through the module 40. For example, in such embodiments, the fibrous member 41 may pass through the defect detection zone 45 contacting substantially opposite sides of the fibrous member 41 with the contacting members 42 and 44. In such embodiments, a defect, e.g., defect 41a, may cause the shifting of the second fiber contacting member 44 away from the first fiber contacting member 42, which may be sensed by the sensor 46. Further, in such embodiments, the sensor 46 may continuously or intermittently generate and/or transmit an electronic signal 46a to communicate a parameter sensed by the sensor 46 to a data processing system or an operator.

Figure 5:
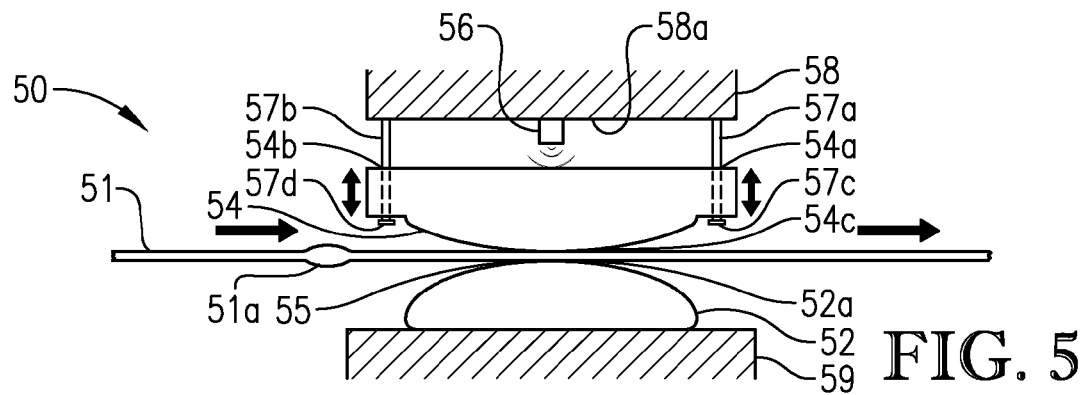
FIG. 5 is a side view of a defect detection module in accordance with yet another embodiment of the present invention, particularly showing a first fiber contacting member secured to a first rigid member, a second fiber contact member shiftably coupled to two pins that are attached to a second rigid member, a sensor coupled to the second rigid member, and a fibrous member positioned between the first and second fiber contacting members.

FIG. 5 depicts one embodiment of a defect detection module 50 that can include a first fiber contacting member 52, a second fiber contacting member 54, and a sensor 56. In certain embodiments, the contacting members 52 and 54 may be made from any material, such as, for example, a metal material, a plastic material, a ceramic material, or a combination thereof.

In the embodiment depicted in FIG. 5, the first fiber contacting member 52 may be coupled to a rigid member 59. The contacting member 52 may be coupled to the rigid member 59 in any manner as long as the contacting member 52 can be coupled thereto in a fixed position. In certain embodiments, the second fiber contacting member 54 may be coupled to a rigid member 58 via pins 57a and 57b. The pins 57a and 57b can be any type of pins as long as the contacting member 54 can shift relative to the rigid member 58. In the embodiment depicted in FIG. 5, the contacting member 54 can include openings 54a and 54b to receive the pins 57a and 57b, respectively. In such embodiments, the openings 54a and 54b may be configured so that the contacting member 54 may slide along the pins 57a and 57b. In one or more embodiments, the rigid members 58 and/or 59 may be components of a multi-fiber production system, such as, for example, a rigid surface of a fiber producing machine or a fiber combining machine, or the rigid members 58 and/or 59 may be a portion of a rigid base of the defect detection module 50 not shown in FIG. 5.

In one or more embodiments, the contacting members 52 and 54 may be biased towards one another. For example, in the embodiment depicted in FIG. 5, the second contacting member 54 may be biased toward the first contacting member 52 via gravity, as the weight of the contacting member 54 may cause the contacting member 54 to shift down along the pins 57a and 57b and be maintained in such a position via the pin heads 57c and 57d.

In certain embodiments, at least a portion of the contacting members 52 and 54 may define a defect detection zone 55 that is configured to receive at least a portion of a fibrous member 51 in a manner such that the fibrous member 51 contacts both contacting members 52 and 54. For example, as shown in the embodiment depicted in FIG. 5, a portion of the contacting members 52 and 54 each present a convex surface 52a and 54c, respectively, that is in contact with the fibrous member 51 as the fibrous member 51 passes through the defect detection zone 55.

As discussed above, the defect detection module 50 of FIG. 5 may include a sensor 56. In certain embodiments, the sensor 56 may have the same properties and parameters as the sensor 36 of the defect detection module 30 discussed above with reference to FIG. 3. In the embodiment depicted in FIG. 5, the sensor 56 can be coupled to the surface 58a of rigid member 58 that faces the contacting member 54. The sensor 56 of FIG. 5 may be placed in any other position as long as the sensor 56 is capable of detecting the movement of the contacting member 54.

In certain embodiments, the defect detection module 50 can be configured to detect a defect, e.g., defect 51a, in the fibrous member 51 as the fibrous member 51 passes through the module 50. For example, in such embodiments, the fibrous member 51 may pass through the defect detection zone 55 contacting substantially opposite sides of the fibrous member 51 with the contacting members 52 and 54. In such embodiments, a defect, e.g., defect 51a, may cause the shifting of the second fiber contacting member 54 up and away from the first fiber contacting member 52, which may be sensed by the sensor 56. Further, in such embodiments, the sensor 56 may continuously or intermittently generate and/or transmit an electronic signal to communicate a parameter sensed by the sensor 56 to a data processing system or an operator.

Figure 6:
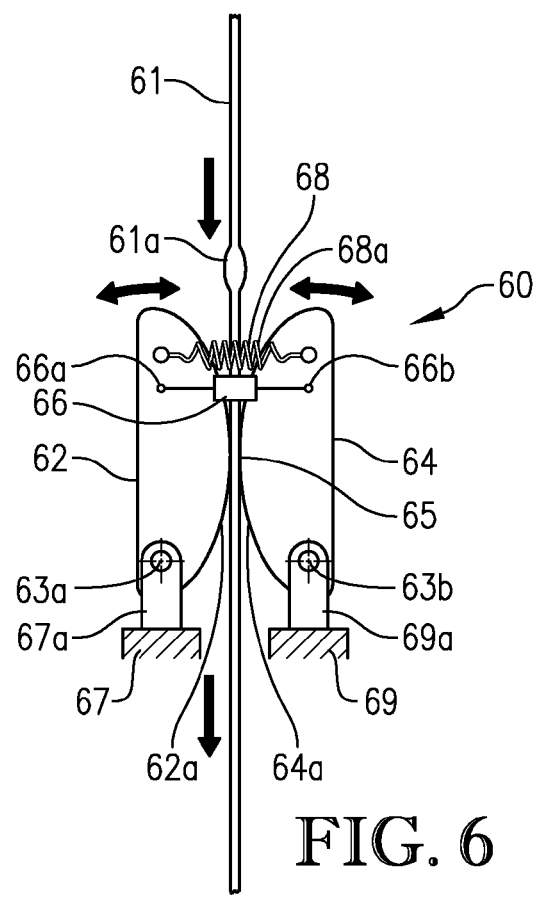
FIG. 6 is a side view of a defect detection module in accordance with one embodiment of the present invention, particularly showing a first fiber contacting member pivotally coupled to a first rigid member, a second fiber contacting member pivotally coupled to a second rigid member, a biasing member coupled to the first and second fiber contacting members, a sensor coupled to the first and second fiber contacting members, and a fibrous member positioned between the first and second fiber contacting members.
Figure 7:
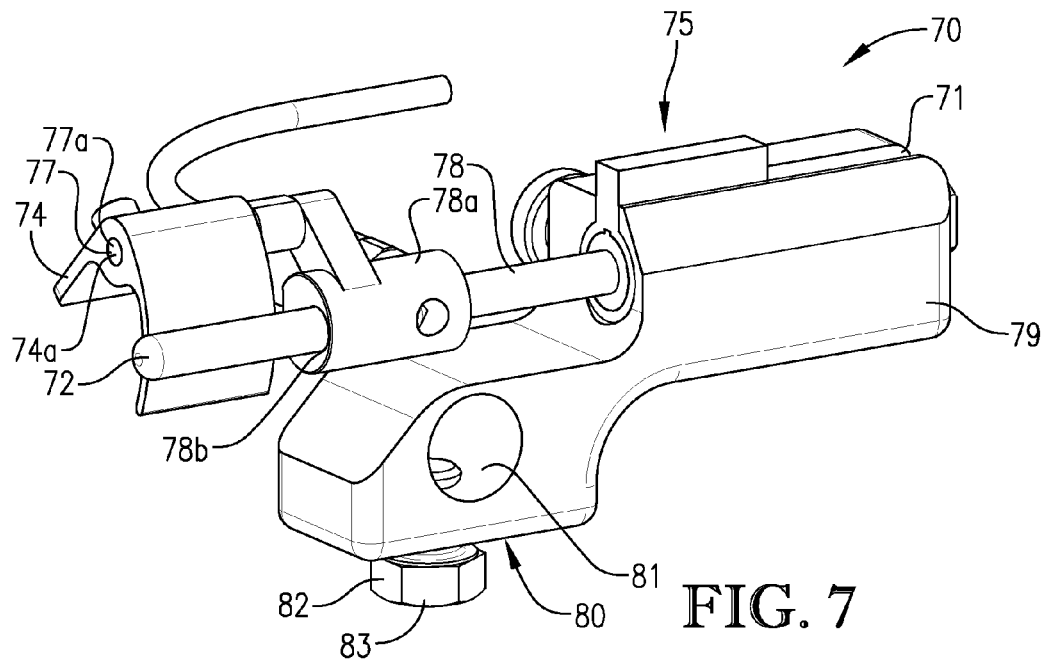
FIG. 7 is a top and side perspective view of a defect detection module in accordance with one embodiment of the present invention, particularly showing a base member having an attachment device positioned near the bottom of the base member, a coupling member secured to an elongated support member, a first fiber contacting member coupled to the elongated support member via the coupling member, and a second fiber contacting member pivotally coupled to the coupling member.

FIG. 6 depicts another embodiment of a defect detection module 60 that may include a first fiber contacting member 62, a second fiber contacting member 64, a sensor 66, and a biasing member 68. The contacting members 62 and 64 may be made from any material, such as, for example, a metal material, a plastic material, a ceramic material, or a combination thereof.

In the embodiment depicted in FIG. 6, the contacting members 62 and 64 may be pivotally coupled to rigid members 67 and 69, respectively, via hinges 63a and 63b. In such embodiments, the hinges 63a and 63b may allow the contacting members 62 and 64, respectively, to move toward and away from one another. The hinges 63a and 63b of FIG. 6 can be any type of hinges as long as the contacting members 62 and 64 are free to move toward and away from one another. In certain embodiments, the rigid members 67 and/or 69 may be components of a multi-fiber production system, such as, for example, a rigid surface of a fiber producing machine or a fiber combining machine, or the rigid members 67 and/or 69 may be a portion of a rigid base of the defect detection module 60 not shown in FIG. 6. In one or more embodiments, the rigid members 67 and 69 of FIG. 6 may include hinge extension members 67a and 69a, respectively, to thereby provide a space for the contacting members 62 and 64 to freely pivot without contacting the rigid members 67 and 69. In certain embodiments, the hinge extension members 67a and 69a can have the same properties and parameters as those discussed above with respect to the hinge extension member 49a of FIG. 4.

As discussed above, the defect detection system 60 may include a biasing member 68. In certain embodiments, such as that depicted in FIG. 6, the biasing member 68 may bias the contacting members 62 and 64 toward one another. The biasing member 68 of FIG. 6 may include a spring 68a that may be coupled to both contacting members 62 and 64. The biasing member 68 may include any type of device capable of causing the contacting members 62 and 64 to be biased toward one another.

In one or more embodiments, at least a portion of the contacting members 62 and 64 may define a defect detection zone 65 that can be configured to receive at least a portion of a fibrous member 61 in a manner such that the fibrous member 61 contacts both contact members 62 and 64. For example, as shown in the embodiment depicted in FIG. 6, a portion of the contacting members 62 and 64 each present a convex surface 62*a* and 64*a*, respectively, that is in contact with the fibrous member 61 as the fibrous member 61 passes through the defect detection zone 65.

As discussed above, the defect detection module 60 of FIG. 6 may include a sensor 66. In certain embodiments, the sensor 66 may have the same properties and parameters as the sensor 36 of the defect detection module 30 discussed above with reference to FIG. 3. In the embodiment depicted in FIG. 6, the sensor 66 may be coupled to both contacting members 62 and 64. In certain embodiments, the sensor 66 may include attachment members 66*a* and 66*b* to attach to the contacting members 62 and 64. The attachment members 66*a* and 66*b* can be any type of attachment members, such as, for example, a screw or pin. The sensor 66 of FIG. 6 may be placed on any other position of the defect detection module 60 as long as the sensor 66 is capable of detecting the movement of the contacting members 62 and 64.

In certain embodiments, the defect detection module 60 may be configured to detect a defect, e.g., defect 61*a*, in the fibrous member 61 as the fibrous member 61 passes through the defect detection zone 65. For example, in such embodiments, the fibrous member 61 may pass through the defect detection zone 65 contacting substantially opposite sides of the fibrous member 61 with the contacting members 62 and 64. In such embodiments, a defect, e.g., defect 61*a*, may cause the shifting of the contacting members 62 and 64 away from one another. Further, in such embodiments, the sensor 66 may continuously or intermittently generate and/or transmit an electronic signal to communicate a parameter sensed by the sensor 66 to a data processing system or an operator.

FIGS. 7-10 depict one embodiment of a defect detection module 70 that can include a first fiber contacting member 72, a second fiber contacting member 74, an elongated support member 78, and a base 79. The base 79, the contacting members 72 and 74, and the elongated support member 78 may be made from any material, such as, for example, a metal material, a plastic material, a ceramic material, or a combination thereof.

In certain embodiments, the base 79 may include an attachment mechanism 80 for securing the defect detection module 70 to a rigid structure, such as, for example, a rigid structure within a fiber producing machine or a fiber combining machine, or a defect detection module support member coupled to at least a portion of a multi-fiber production system. In one or more embodiments, the attachment mechanism 80 may include a through-opening 81 extending through the base 79, which may receive at least a portion of the aforementioned rigid structure. Further, in such embodiments, the attachment mechanism 80 may include a securing device 82 configured to secure the module 70 to at least a portion of the rigid structure discussed above. For example, in various embodiments not depicted in the Figures, the through-opening 81 may receive at least a portion of a defect detection module support member coupled to at least a portion of a multi-fiber production system, with the securing device 82 securing the module 70 thereto. The securing device 82 may be any type of device capable of securing an object inside at least a portion of the through-opening 81. In the embodiment depicted in FIG. 7, the securing device 82 may include a bolt 83 that extends through the base 79 and into the through-opening 81.

In certain embodiments, the elongated support member 78 of FIGS. 7-10 may be coupled to the base 79. For example, as discussed below with respect to FIG. 10, the elongated support member 78 may be coupled to a groove 71 in the base 79 via a base coupling member 75. Further, as will be discussed in detail below with respect to FIG. 10, the elongated support member 78 may include a coupling region 78*a* configured to connect the elongated support member 78 to the contacting members 72 and 74. The elongated support member 78 may be any size and shape, as long as the support member 78 is capable of connecting the contacting members 72 and 74 thereto while being secured to the base 79.

Figure 8:
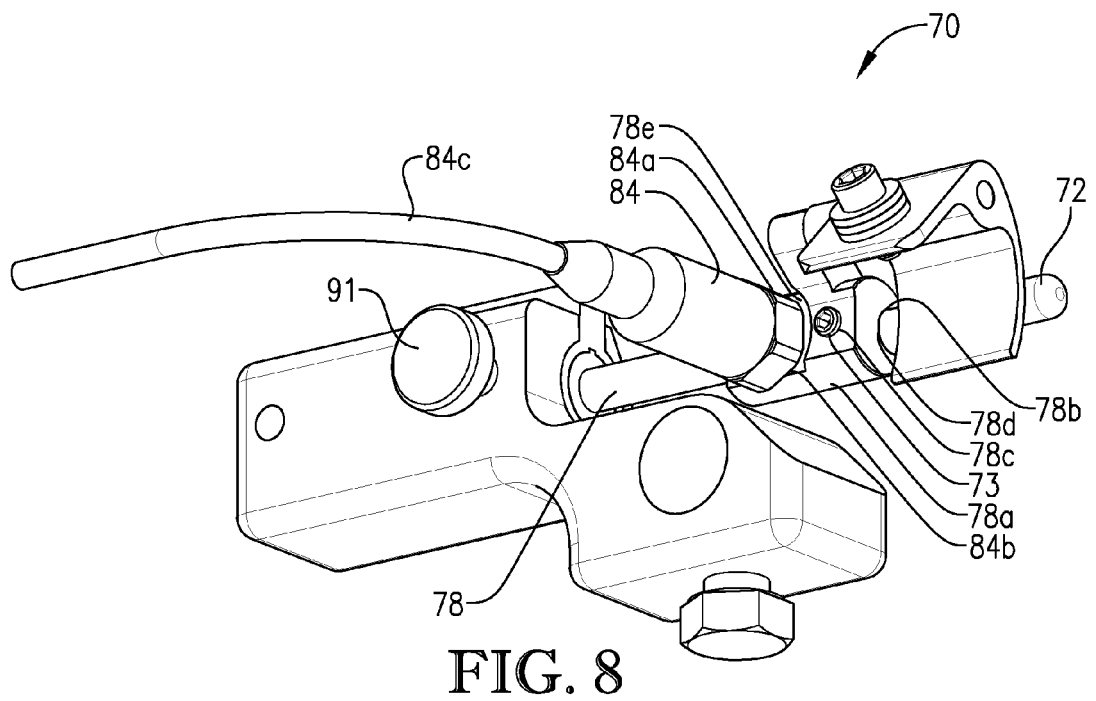
FIG. 8 is a bottom and side perspective view of the defect detection module of FIG. 7, particularly showing a sensor attached to the coupling member, and a biasing member coupled to the second fiber contacting member.
Figure 10:
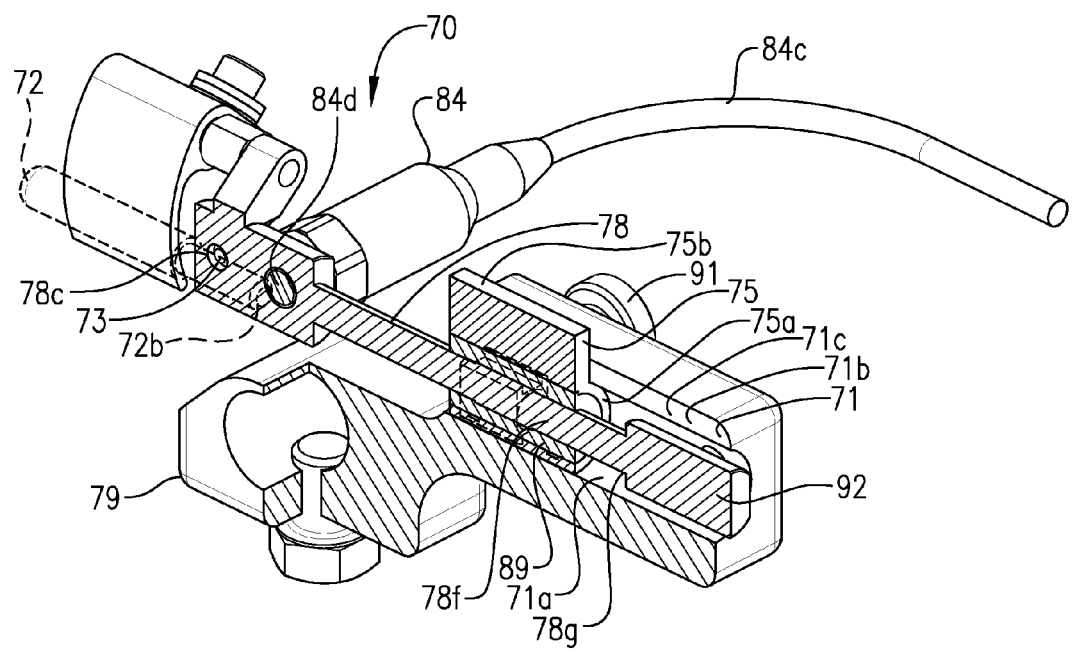
FIG. 10 is a top perspective and cross-sectional view of the defect detection module of FIG. 7, particularly showing a counter balance at one end of the elongated support member, and a dampening mechanism coupled to both the base member and the elongated support member.

In certain embodiments, the first fiber contacting member 72 may be coupled to the coupling region 78*a* of the elongated support member 78. In such embodiments, at least a portion of the contacting member 72 may be inserted into an opening 78*b* of the elongated support member 78. In certain embodiments, the contacting member 72 may be fixedly secured to the elongated support member 78. The contacting member 72 may be fixedly secured to the elongated support member 78 in any manner known to one skilled in the art. For example, as depicted in FIGS. 8 and 10, the contacting member 72 may be secured to the elongated support member 78 via a fastener 73 extending through an opening 78*c* in the elongated support member 78. In the embodiment depicted in FIG. 8, the fastener 73 may apply a force to at least a portion of the contacting member 72 so that at least a portion of the contacting member 72 is secured against an inner wall 78*d* of the opening 78*b*.

In one or more embodiments, the second fiber contacting member 74 may be pivotally coupled to the elongated support member 78. For example, in the embodiment depicted in FIG. 7, the contacting member 74 may be coupled to the coupling region 78*a* of the elongated support member 78 via a hinge 77. The hinge 77 may be any type of hinge as long as it is capable of coupling the contacting member 74 to the elongated support member 78 in a manner that allows the contacting member 74 to shift about the hinge 77. For example, in the embodiment depicted in FIG. 7, the hinge 77 may include a protrusion 77*a* extending out from the coupling region 78*a* of the elongated support member 78, and the contacting member 74 may include an opening 74*a* configured to receive at least a portion of the protrusion 77*a*, thereby allowing the contacting member 78 to shift about the protrusion 77*a*. In certain embodiments, the protrusion 77*a* may be integral with the elongated support member 78. In certain other embodiments, the protrusion 77*a* may be coupled to the elongated support member 78.

In certain embodiments, the defect detection module 70 of FIGS. 7-10 may include a sensor 84. The sensor 84 may have the same parameters and properties as the sensor 36 discussed above with reference to the defect detection module 30 of FIG. 3. For example, in certain embodiments, the sensor 84 may include an accelerometer. In one or more embodiments, the sensor 84 may be coupled to the elongated support member 78. For example, in the embodiment depicted in FIG. 8, the sensor 84 may be coupled to the coupling region 78*a* of the elongated support member 78. The sensor 84 may be coupled to the elongated support member 78 in any manner known to one skilled in the art, as long as the sensor 84 is capable of monitoring a fibrous member in such a manner so as to be able to detect a defect in that fibrous member. For example, in certain embodiments, the sensor 84 may be stud mounted via a stud 84*a* to a flat region 78*e* of the coupling region 78*a*, with the surface 84*b* of the stud 84*a* flush against the flat region 78*e*. In certain embodiments, the sensor 84 may be coupled to a cable 84*c* to electronically transmit sensed information from the defect detection module 70 to a data processing system or an operator.

Figure 9:
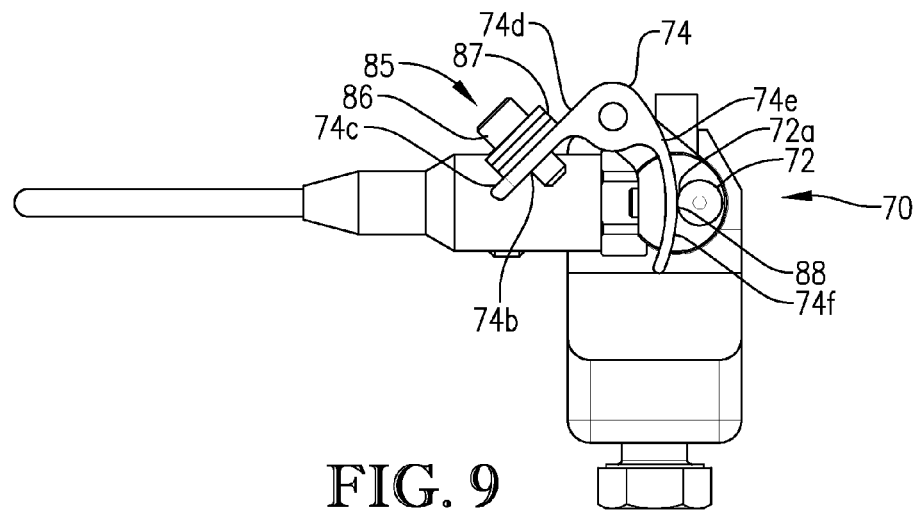
FIG. 9 is a side view of the defect detection module of FIG. 7, particularly showing the first and second fiber contact members biased toward one another, and a defect detection zone defined by a portion of the first and second fiber contacting members.

As best can be seen in the FIG. 9, in one or more embodiments, the defect detection module 70 may include a biasing member 85 so that the contacting members 72 and 74 are biased toward one another. In certain embodiments, the biasing member 85 of FIG. 9 may be coupled to the second fiber contacting member 74. For example, the biasing member 85 of FIG. 9 may include a bolt 86 that extends through a through-opening 74*b* of the contacting member 74 with plurality of washers 87 positioned over the bolt 86 on the outer surface 74*c* of the biasing region 74*d* of the contacting member 74. Due to the force of gravity, the weight of the washers 87 on the outer surface 74*c* of the biasing region 74*d* of the contacting member 74 can cause the contact region 74*e* of the contacting member 74 to be biased towards the contacting member 72. In certain embodiments, an operator may apply any number of washers 87 to the biasing member 85 to provide the appropriate level of force to the second fiber contacting member 74. The biasing member 85 may include any mechanism capable of biasing the contacting members 72 and 74 toward one another, and a specific mechanism can be chosen by one skilled in the art for a particular purpose.

In one or more embodiments, such as that depicted in FIG. 9, at least a portion of the contacting members 72 and 74 may define a defect detection zone 88 that is configured to receive at least a portion of a fibrous member in a manner such that the fibrous member contacts both contacting members 72 and 74. For example, as shown in the embodiment depicted in FIG. 9, the biasing member 85 may cause the contacting members 72 and 74 to be in close proximity or in contact with one another such that a fibrous member may contact a convex surface 72*a* of the first fiber contacting member 72 while simultaneously contacting a convex surface 74*f* of the second fiber contacting member 74.

As discussed above, the elongated support member 78 of FIGS. 7-10 may be coupled to the base 79 via a base coupling member 75. As best seen in the embodiment depicted in FIG. 10, the base coupling member 75 may receive a portion 78*f* of the elongated support member 78 inside a hollow, roughly circular portion 75*a* of the base coupling member 75 that is positioned inside the groove 71 of the base 79. For example, the roughly circular portion 75*a* of the base coupling member 75 may be complimentary in shape to the roughly circular bottom surface 71*a* of the groove 71, while a protrusion 75*b* of the base coupling member 75 may extend out from the roughly circular region 75*a* of the base coupling member 75, and extend out of the opening 71*b* in the groove 71 and contact the top inner surface 71*c* of the groove 71. The base coupling member 75 and the groove 71 of the base 79 may be any complimentary shape and/or size as long as the elongated support member 78 is securely coupled to the base 79.

In certain embodiments, the defect detection module 70 may include a fastener 91 to secure the base coupling member 75 to the base 79. For example, in the embodiment depicted in FIGS. 8 and 10, the fastener 91 may extend through the base 79 and into the groove 71 to apply a force to the base coupling member 75, thereby holding the base coupling member 75 against the bottom surface 71*a* of the groove 71 of the base 79.

In certain embodiments, the defect detection module 70 may include a dampening member 89 configured to minimize any background vibration coming from any component of a multi-fiber article production system and transmitted through the base 79. For example, in the embodiment depicted in FIG. 10, the defect detection module 70 may include a dampening member 89 encompassing the portion 78*f* of the elongated support member 78 positioned inside the circular region 75*a* of the base coupling member 75. The dampening member may include any type of material that is capable of minimizing any background vibrations. For example, in certain embodiments, the dampening material may include a silicone material, a rubber material, or a combination thereof.

In one or more embodiments, the defect detection module 70 may include a counter balance 92 that may provide added stability to the defect detection module 70 during operation. For example, in the embodiment depicted in FIG. 10, the counter balance 92 may be coupled to the end 78*g* of the elongated support member 78 opposite where the contacting members 72 and 74 are positioned. In the embodiment depicted in FIG. 10, the counter balance 92 may be integral with the elongated support member 78. In certain other embodiments, the counter balance 92 may be a separate material coupled to the end 78*g* of the elongated support member 78.

In certain embodiments, the defect detection module 70 may be configured to monitor a fibrous member via the contacting members 72 and 74. For example, as discussed above, in one or more embodiments, a fibrous member may contact both contacting members 72 and 74 as the fibrous member passes through the defect detection zone 88. In such embodiments, as discussed above, the first fiber contacting member 72 may be coupled to the elongated support member 78 by being inserted into an opening 78*b* of the elongated support member 78. As best seen in the embodiment depicted in FIG. 10, the end 72*b* of the contacting member 72 inside the elongated support member 78 may be adjacent to a portion 84*d* of the sensor 84. In such embodiments, the sensor 84 may be in a position to closely monitor the movement or shifting of the first fiber contacting member 72 as the fibrous member contacts the fiber contacting member 72.

In certain embodiments, after the sensor 84 senses the shifting of one of the contacting members 72 or 74 relative to the other of the contacting members 72 or 74, and generates an electronic signal based on that sensed shifting, that electronic signal may be processed to yield real-time data about the quality of a fibrous member, e.g., the width of the fibrous member. In such embodiments, a defect warning may be activated when the real-time data indicates a defect, e.g., a variation in the width of the fibrous member. Further, in such embodiments, the defect warning may be selected from the group consisting of an audible warning, a visual warning, automatically shutting down one or more items of equipment, and combinations thereof.

As discussed above, in certain embodiments, the sensor, e.g., sensor 84, may be connected to a data processing system, e.g., the data processing system 24 of FIG. 2. The sensor 84 may be connected to a data processing system in any manner known to one skilled in the art, and a particular connection system may be chosen for a specific purpose. In certain embodiments, the sensor cable 84*c* may be terminated by a quick connect/disconnect RF connector, such as, for example, a Bayonet Neill-Concelman ("BNC") connector. In such embodiments, the sensor cable 84*c* may be connected directly to a data acquisition module, e.g., a National Instruments NI 9234 module having four analog inputs. Further, in such embodiments, the data acquisition module may be coupled to a chassis designed for sensor measurement systems having at least one counter/timer built into the chassis, such as, for example, a National Instruments NI cDAQ-9171 USB chassis. In such embodiments, the chassis may be connected, via a USB port, to a computer having a processor and memory. In addition, in such embodiments, data acquisition software may be written to acquire the data from the sensor 84. Any type of data acquisition software known to one skilled in the art may be written or utilized. In certain embodiments, one may use the LabVIEW system design software from National Instruments to write the data acquisition software. Further, in such embodiments, data from the sensor 84 may be acquired at any rate, such as, for example, a rate of 100 or 1000 samples per second. In certain embodiments, once the data is acquired by the data processing system, it may be dynamically displayed in a program, e.g., a LabVIEW program, plotted in a spreadsheet manually, and/or processed dynamically to allow software to determine if a defect, e.g., spinning machine harsh, is present.

In one or more embodiments, a data processing system, e.g., the data processing system 24 of FIG. 2, may accommodate data from at least 10, 15, or 20 individual defect detection modules. For example, in certain embodiments, the data processing system, e.g., the data processing system 24 of FIG. 2, may include at least 2, 3, or 4 data acquisition modules, such as, for example, National Instruments NI 9234 modules having four analogue inputs. Further, in such embodiments, the data processing system, e.g., the data processing system 24 of FIG. 2, may include a device for data acquisition and processing, such as, for example, a National Instruments NI cRIO-9082 multicore system, which can connect with multiple data acquisition modules. In such embodiments, the data processing system, e.g., the data processing system 24 of FIG. 2, may be configured to acquire and simultaneously process data from all the individual defect detection modules connected thereto. In certain embodiments, the data processing system, e.g., the data processing system 24 of FIG. 2, may be configured in any manner known to one skilled in the art as long as the data processing system is capable of simultaneously acquiring and analyzing data from any number of individual defect detection modules connected thereto.

In certain embodiments, the data processing system, e.g., the data processing system 24 of FIG. 2, may include a system and/or a process for detecting and/or notifying an operator when a defect, e.g., spinning machine harsh, is present in a fibrous member. In such embodiments, the system and/or process may include monitoring data acquired from the sensor 84, e.g., data from an accelerometer for a given period of time. In certain embodiments, the system and/or process may include monitoring the last twenty seconds of data from the sensor 84. Further, in such embodiments, the system and/or process may include calculating the average of the data set, such as, for example, the last twenty seconds of data or a specified number of data points, e.g., the last 2000 data points. In such embodiments, a threshold value may then be calculated, which may be the average plus or minus ten times the standard deviation of the data set, e.g., the last 2000 data points. Next, in such embodiments, if any of the data points are outside this threshold value then the entire data set may be stored, e.g., on a hard drive of a computer. Further, in such embodiments, if a data point is outside the threshold value and the data set is stored, the data processing system may initiate a delay, e.g., a ten second delay, where no further data is stored. In certain embodiments, such a delay may be necessary in order to avoid storing hundreds or thousands of files for every single data point outside the threshold value. Next, in such embodiments, the number of data points outside the threshold value for a given data set is calculated and, based on that number, the system and/or process may decide if a defect in the fibrous member, e.g., spinning machine harsh, is present, potentially present, or not present.

Figure 11:
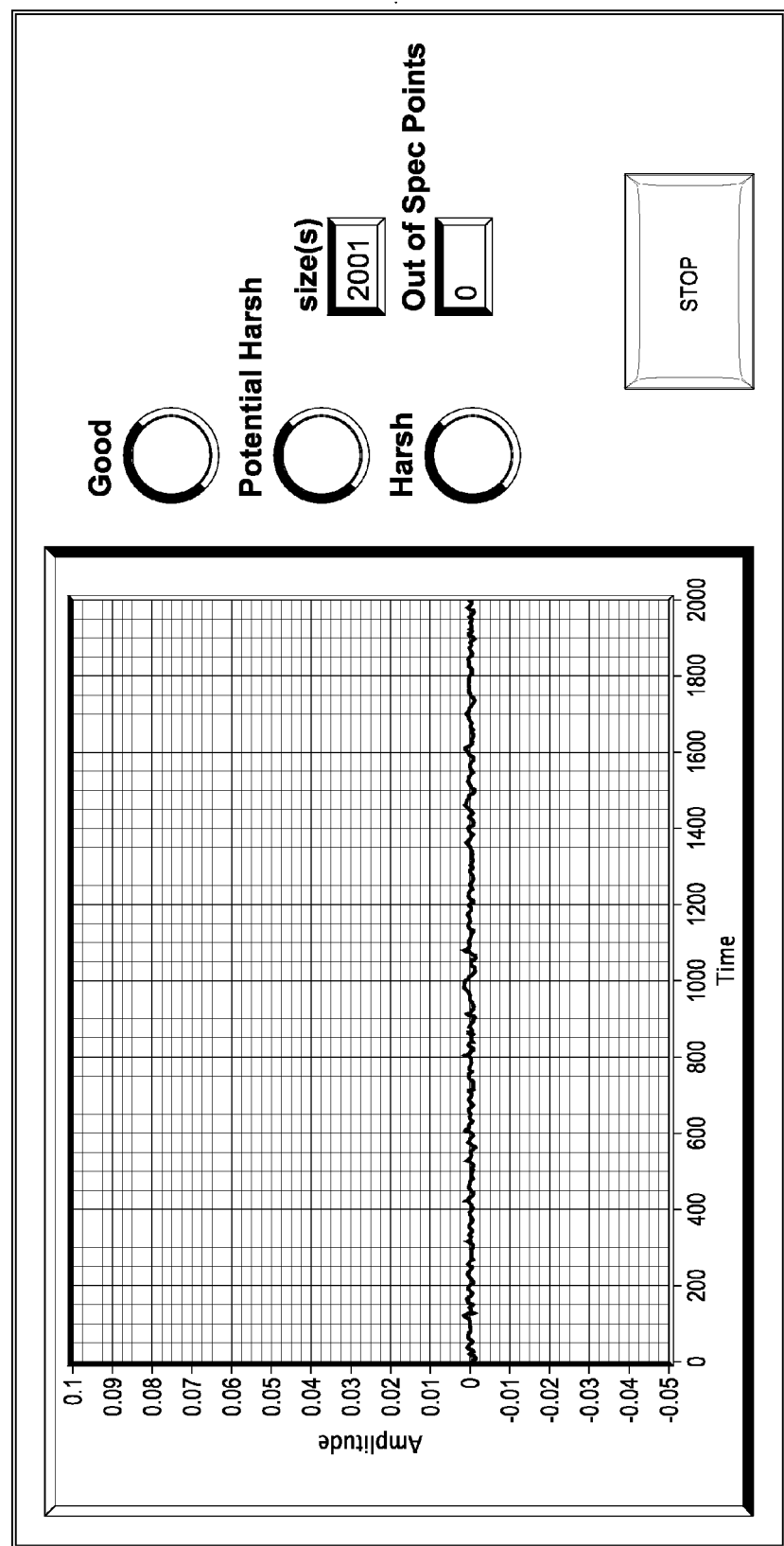
FIG. 11 is an exemplary illustration of a user interface that may be produced by a data processing system according to one embodiment of the present invention, particularly showing the user interface when no harsh may be detected.
Figure 12:
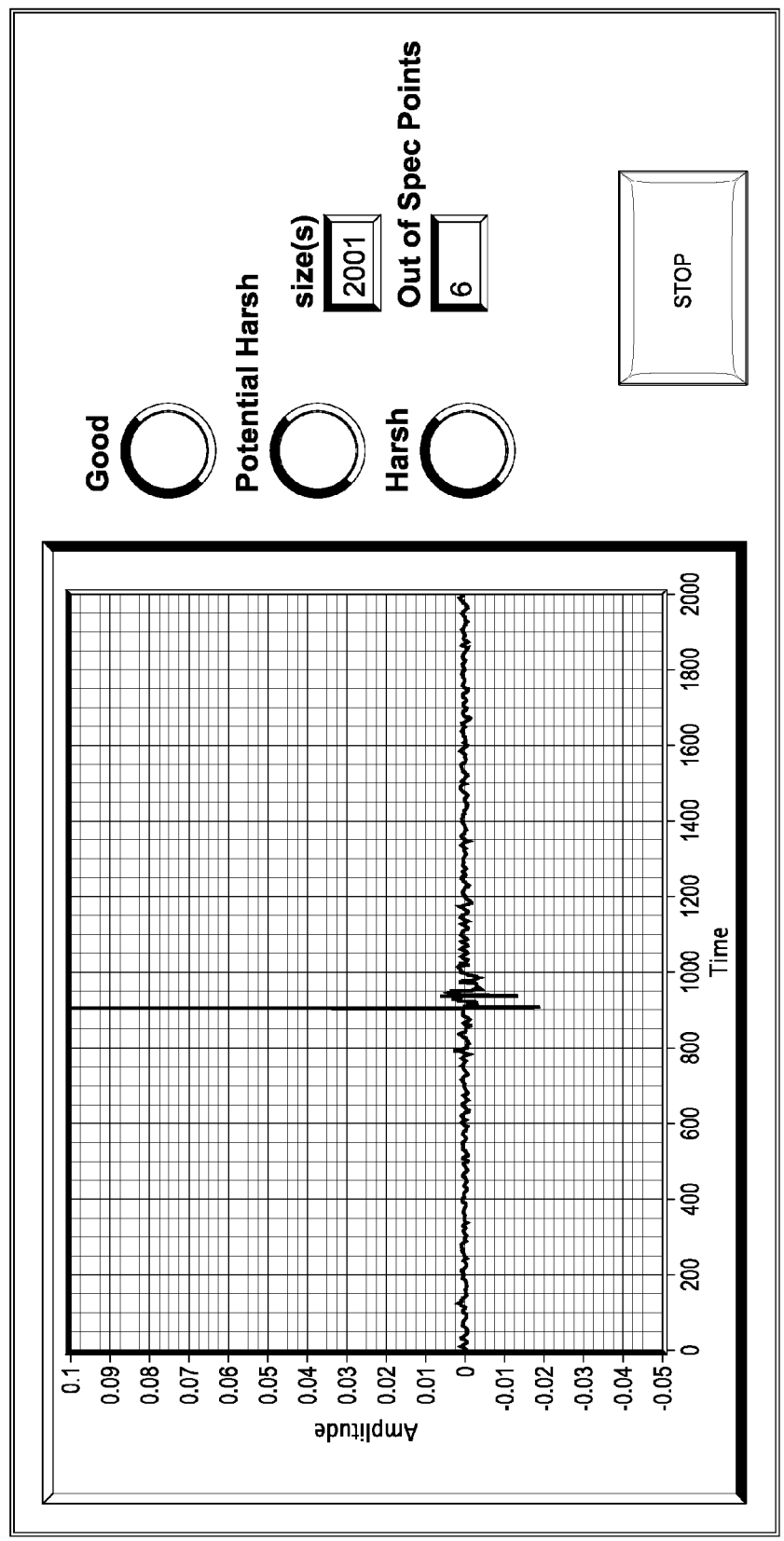
FIG. 12 is an exemplary illustration of a user interface that may be produced by a data processing system according to one embodiment of the present invention, particularly showing the user interface when potential harsh may be detected.
Figure 13:
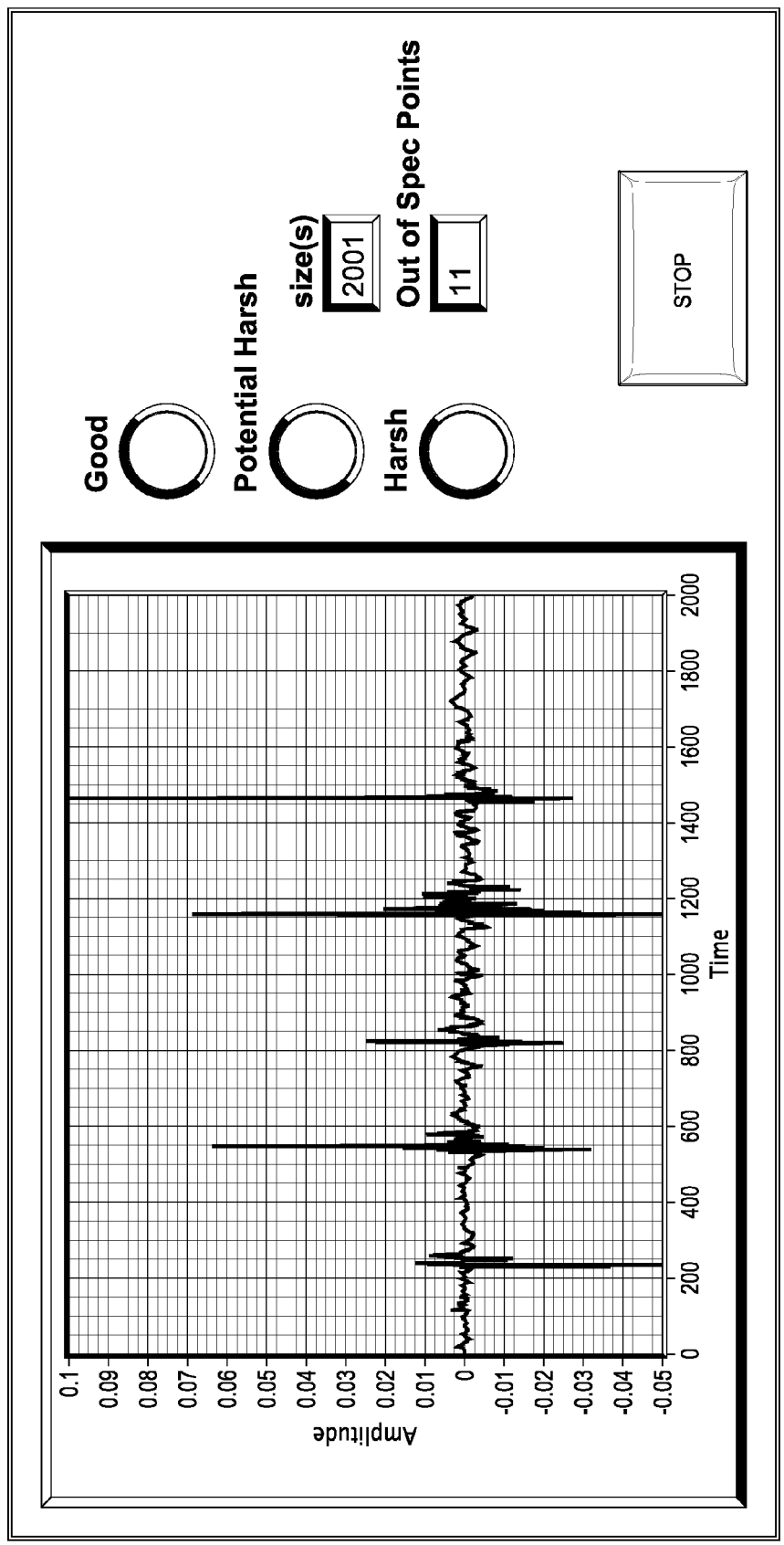
FIG. 13 is an exemplary illustration of a user interface that may be produced by a data processing system according to one embodiment of the present invention, particularly showing the user interface when harsh may be detected.

FIGS. 11-13 provide exemplary views of a user interface an operator may see as an output for the above described data processing system, which may display the processed data and also notify the operator as to whether a defect is present, potentially present, or not present. In certain embodiments, as seen in the exemplary view of the user interface depicted in FIG. 11, a system may display a data set of 2001 data points where none of the specific data points are outside a calculated threshold value, and thus, the system may indicate that the multi-fiber production system is "good" or that no defect is present. In one or more embodiments, as seen in the exemplary view depicted in FIG. 12, a system may display a data set of 2001 data points where 6 specific data points are outside a calculated threshold value, and thus, the system may indicate that the multi-fiber production system has "potential harsh," or a potential defect. In certain embodiments, as seen in the exemplary view depicted in FIG. 13, a system may display a data set of 2001 data points where 11 specific data points are outside a calculated threshold value, and thus, the system may indicate that the multi-fiber production system has "harsh," or a defect. In one or more embodiments, such as those depicted in FIGS. 11-13, a system may provide a "stop" button on a user interface for an operator to stop all or a portion of the multi-fiber article production process based on the information obtained and processed from at least one sensor, e.g., sensor 84. In certain embodiments, the system and/or process may include the use of software, e.g., LabVIEW software from National Instruments, to automate at least a portion of the system and/or process described above and provide a user interface, such as that depicted in FIGS. 11-13.

This invention can be further illustrated by the following examples of embodiments thereof, although it will be understood that these examples are included merely for the purposes of illustration and are not intended to limit the scope of the invention unless otherwise specifically indicated.

EXAMPLES

Example 1

Detection of Spinning Machine Harsh

A spinning cabinet for forming a cellulose acetate tow that exhibited spinning machine harsh was identified by manual inspection. The defect detection module 70 depicted in FIGS. 7-10, was temporarily installed on that spinning cabinet and connected to a data processing system. An integrated electronics piezo electric based accelerometer was used as the sensor. The data processing system utilized is described above with respect to the data processing system 24 of FIG. 2. Specifically, the accelerometer cable was connected to National Instruments NI 9234 module having four analog inputs, which in turn, was coupled to a National Instruments NI cDAQ-9171 USB chassis. Data was acquired at a rate of 100 or 1000 samples per second.

The data acquisition software was written in the LabVIEW language. Once the data was acquired, it was manually added to a spreadsheet. The data is displayed in FIG. 14.

Further, a spinning cabinet for forming cellulose acetate tow was manually inspected and determined to have no spinning machine harsh. This cabinet was fitted with the same defect detection module used in generating the data provided in FIG. 14, and the data for this cabinet was similarly displayed as shown in FIG. 15.

Figure 14:
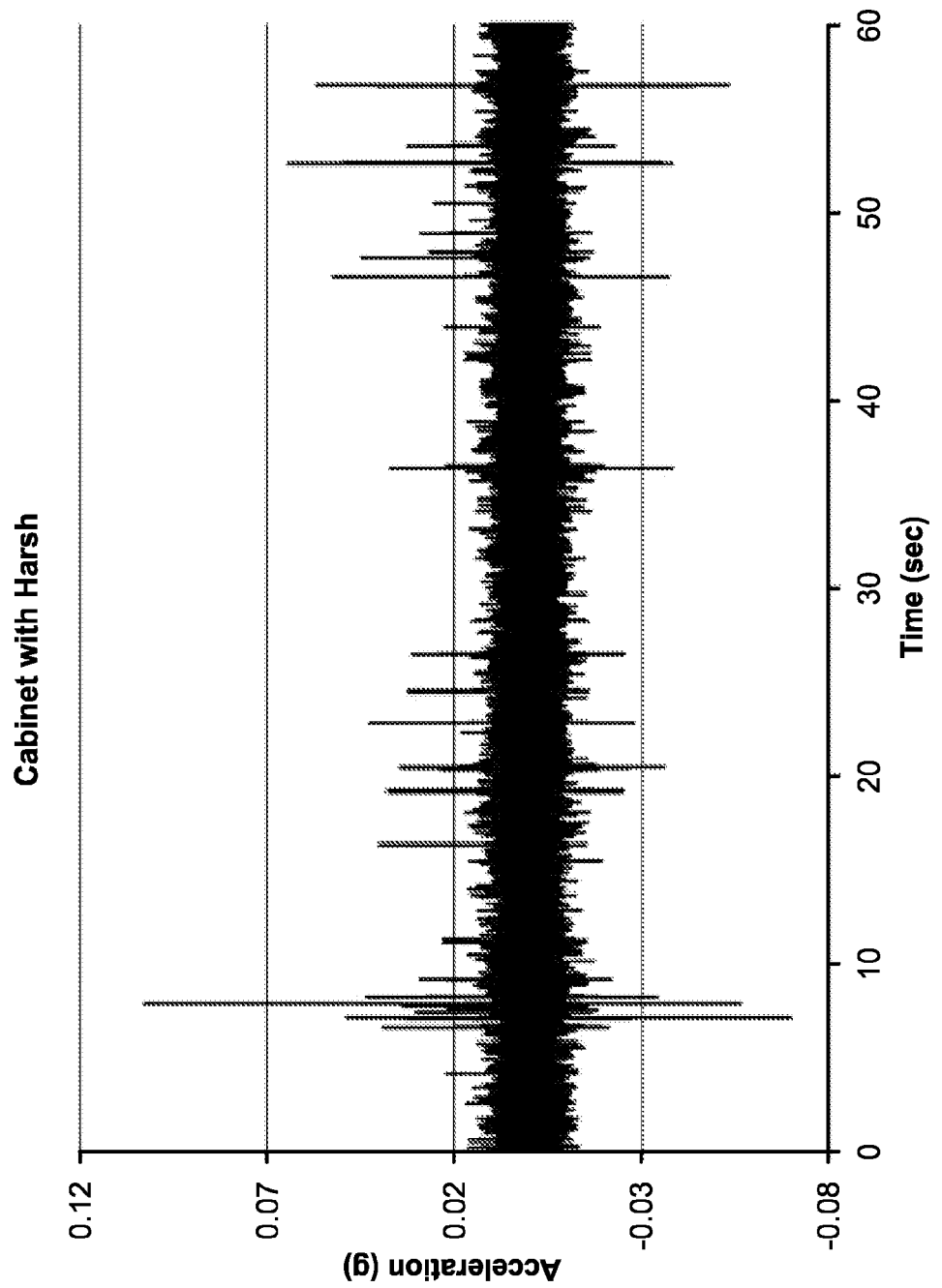
FIG. 14 is a graph depicting accelerometer data obtained on a spinning cabinet exhibiting harsh.
Figure 15:
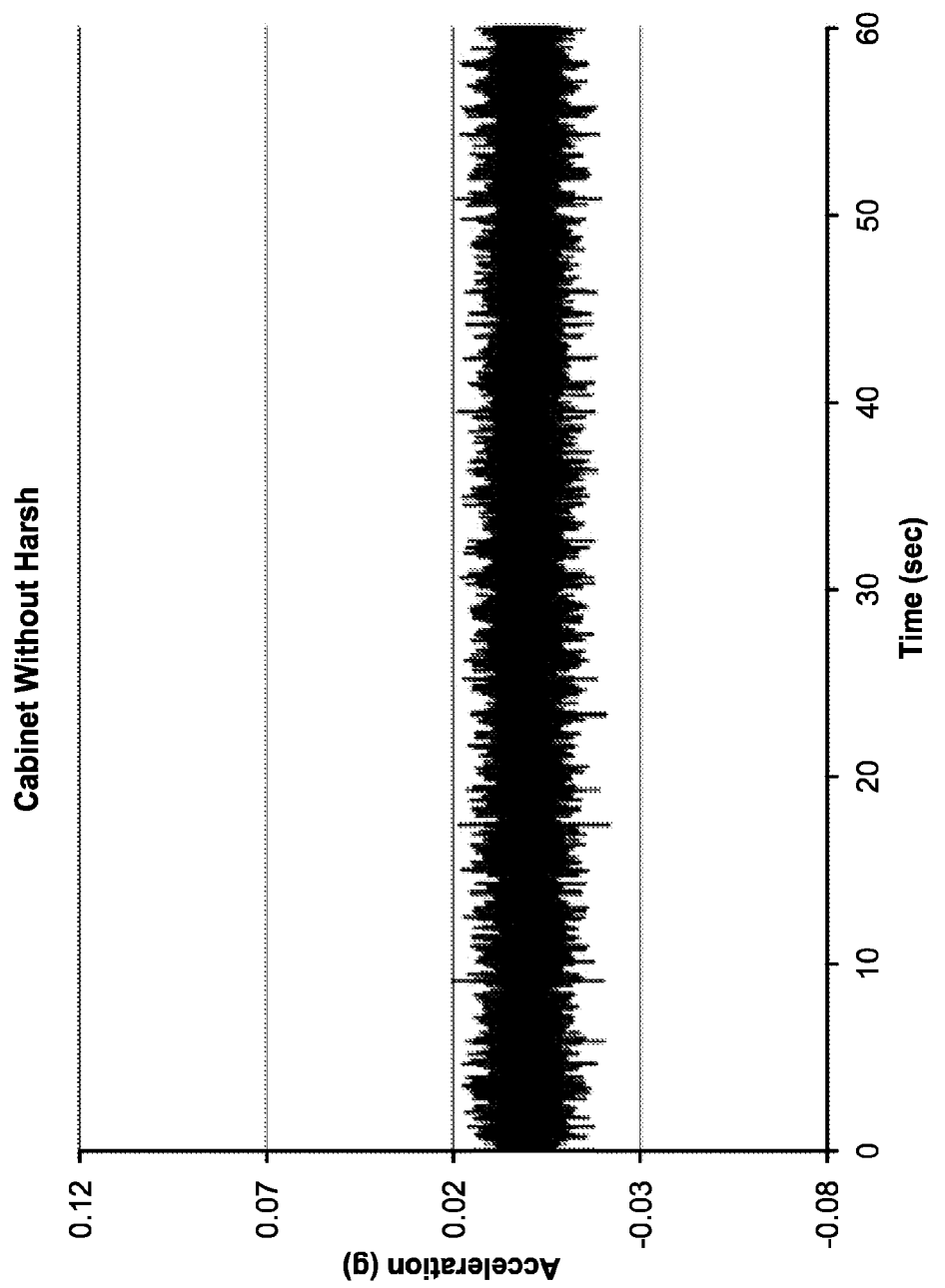
FIG. 15 is a graph depicting accelerometer data obtained on a spinning cabinet exhibiting no harsh.

As can be seen in FIG. 14, the data obtained from the spinning cabinet manually detected to have spinning machine harsh exhibits several spikes outside the range of the majority of the data obtained from that cabinet, which is consistent with the presence of spinning machine harsh. Further, as can be seen in FIG. 15, the data obtained from the spinning cabinet manually determined to not be exhibiting spinning machine harsh does not exhibit the data spikes observed in FIG. 14, which is consistent with the absence of spinning machine harsh. Therefore, this data demonstrates that the defect detection module utilized in this Example, together with the data processing system 24 utilized, can successfully identify spinning machine harsh in a spinning cabinet.

The preferred forms of the invention described above are to be used as illustration only, and should not be used in a limiting sense to interpret the scope of the present invention. Modifications to the exemplary embodiments, set forth above, could be readily made by those skilled in the art without departing from the spirit of the present invention.

The inventors hereby state their intent to rely on the Doctrine of Equivalents to determine and assess the reasonably fair scope of the present invention as it pertains to any apparatus not materially departing from but outside the literal scope of the invention as set forth in the following claims.

What is claimed is:

1. An on-line defect detection system for detecting a defect in an elongated continuous fibrous member during transferring of said fibrous member from a fiber producing machine to a fiber combining machine, said defect detection system comprising:
   a support member;
   a first fiber contacting member fixed to said support member;
   a second fiber contacting member shiftable relative to said first fiber contacting member;
   a defect detection zone defined between at least a portion of said first and second fiber contacting members, wherein said defect detection zone is configured to receive at least a portion of said fibrous member in a manner such that said fibrous member contacts said first and second fiber contacting members in said defect detection zone; and
   a sensor configured to (i) sense movement of second fiber contacting member and (ii) generate an electronic signal based on the sensed movement of said second fiber contacting member, wherein said sensor is coupled to said support member and wherein said sensor is spaced from and does not contact said second fiber contacting member.

2. The system according to claim 1, further comprising a data processing system for receiving said electronic signal and, based on said electronic signal, determining whether said defect is present in said fibrous member.

3. The system according to claim 1, wherein said defect is characterized by an increased width of said fibrous member.

4. The system according to claim 1, wherein said fibrous member comprises multiple individual filaments.

5. The system according to claim 1, wherein said fibrous member is a tow comprising a plurality of individual filaments.

6. The system according to claim 5, wherein said tow comprises cellulose acetate.

7. The system according to claim 5, wherein said tow is formed of at least 1 and/or not more than 100,000 of said individual filaments.

8. The system according to claim 1, wherein said sensor is selected from the group consisting of an optical sensor, an electromagnetic sensor, an acoustical sensor, a mechanical sensor, an electrical sensor, and a combination thereof.

9. The system according to claim 8, wherein said sensor comprises an accelerometer.

10. The system according to claim 1, wherein said fiber producing machine is a spinning machine.

11. The system according to claim 1, further comprising a dampening member.

12. The system according to claim 1, wherein said first and second fiber contacting members are biased toward one another.

13. The system according to claim 12, wherein said first and second fiber contacting members are gravity biased toward one another.

14. An on-line defect detection process comprising:
   (a) producing a continuous elongated fibrous member in a fiber forming machine;
   (b) passing said fibrous member through a defect detection zone, wherein said passing includes contacting substantially opposite sides of said fibrous member with first and second fiber contacting members, wherein variations in the width of said fibrous member causes shifting of said second fiber contacting member relative to said first fiber contacting member, and wherein said first fiber contacting member is fixed to a support member;
   (c) sensing the shifting of said second fiber contacting member relative to said first fiber contacting member, wherein said sensing is performed with a sensor coupled to said support member and wherein said sensor is spaced from and does not contact said second fiber contacting member; and
   (d) generating an electronic signal based on the sensed shifting of step (c).

15. The process according to claim 14, further comprising processing said electronic signal to yield real-time data about the width of said fibrous member.

16. The process according to claim 15, further comprising activating a defect warning when said real time data indicates an unacceptable variation in the width of said fibrous member, wherein said defect warning is selected from the group consisting of an audible warning, a visual warning, automatically shutting down one or more items of equipment, and combinations thereof.

17. The process according to claim 14, wherein steps (b), (c), and (d) are carried out simultaneously.

18. The process according to claim 14, further comprising, subsequent to step (b), combining a plurality of said fibrous members in a fiber combining machine to produce a multi-fiber article.

19. The process according to claim 14, wherein said fibrous member is a tow comprising a plurality of individual filaments.

20. The process according to claim 19, wherein said tow comprises cellulose acetate.

21. The process according to claim 19, wherein said tow is formed of at least 1 and/or not more than 100,000 of said individual filaments.

22. The process according to claim 14, wherein said fiber producing machine is a spinning machine.

23. The process according to claim 14, wherein said fiber combining machine is configured to produce a multi-fiber article selected from the group consisting of a band, a yarn, a woven article, and a non-woven article.

24. The process according to claim 14, wherein said first and second fiber contacting members are biased toward one another.

25. A multi-fiber article production system comprising:
a fiber source;
at least one spinning machine configured to form at least a portion of said fiber source into a tow;
a tow combining machine configured to combine a plurality of said tows into a tow band,
a support member;
a first tow contacting member fixed to said support member;
a second tow contacting member, wherein said second tow contacting member is shiftable relative to said first tow contacting member;
a defect detection zone defined between at least a portion of said first and second tow contacting members, wherein said defect detection zone is configured to receive at least a portion of said tow in a manner such that said tow contacts said first and second tow contacting members in said defect detection zone; and
a sensor configured to (i) sense movement of said second tow contacting member and (ii) generate an electronic signal based on the sensed movement of said second tow contacting member, wherein said sensor is coupled to said support member and wherein said sensor is spaced from and does not contact said second tow contacting member.

26. The system according to claim 25, wherein said sensor comprises an accelerometer.

27. The system according to claim 25, wherein said first and second tow contacting members are biased toward one another.

28. The system according to claim 25, further comprising a dampening member.

29. The system according to claim 25, wherein said tow comprises a plurality of individual filaments.

30. The system according to claim 29, wherein said tow comprises cellulose acetate.

31. The system according to claim 29, wherein said tow is formed of at least 1 and/or not more than 100,000 of said individual filaments.

32. The system according to claim 25, wherein said defect is spinning machine harsh.

33. The system of claim 1, wherein said system is configured such that movement of said second fiber contacting member causes movement of said first fiber contacting member and said support member.

34. The system of claim 33, wherein said sensor indirectly senses movement of said second fiber contacting member by directly sensing movement of said support member.

35. The system of claim 33, further comprising a dampening member coupled to said support member.

36. The system of claim 35, wherein said support member is an elongated support member, wherein said system further comprises a counter balance coupled to said support member, wherein said dampening member is coupled to said elongated supported member at a location between said counter balance and said first fiber contacting member.

37. The system of claim 1, wherein said second fiber contacting member is spaced from and does not contact said support member.

38. The system of claim 37, wherein said second fiber contacting member is coupled to said first fiber contacting member via a hinge that is spaced from and does not contact said support member.

39. The system of claim 25, wherein said system is configured such that movement of said second tow contacting member causes movement of said first tow contacting member and said support member, wherein said sensor indirectly senses movement of said second tow contacting member by directly sensing movement of said support member.

40. The system of claim 25, wherein said second tow contacting member is coupled to said first tow contacting member via a hinge that is spaced from and does not contact said support member, wherein said support member is an elongated support member, further comprising a dampening member coupled to said elongated support member, further comprising a counter balance coupled to said elongated support member, wherein said dampening member is coupled to said elongated supported member at a location between said counter balance and said first tow contacting member.

* * * * *